United States Patent [19]
Porter

[11] Patent Number: 6,048,303
[45] Date of Patent: Apr. 11, 2000

[54] MAGNETIC FLUX APPLICATION TO TISSUE UTILIZING POLYMERIC STRIP-SHAPED PERMANENT MAGNETS

[76] Inventor: Donald I. Porter, 2767 Blendon Woods Blvd., Columbus, Ohio 43231

[21] Appl. No.: 09/138,044

[22] Filed: Aug. 21, 1998

[51] Int. Cl.$^7$ .................................................... A61B 17/52
[52] U.S. Cl. ............................................................ 600/15
[58] Field of Search ................................. 600/48, 49, 50, 600/51, 52, 53, 54, 55, 9, 10, 11, 12, 13, 14, 15

[56] References Cited

U.S. PATENT DOCUMENTS

| | | |
|---|---|---|
| 645,433 | 3/1900 | Strange et al. . |
| 3,191,106 | 6/1965 | Baermann . |
| 3,518,593 | 6/1970 | Hall . |
| 4,143,435 | 3/1979 | Masuda . |
| 4,330,892 | 5/1982 | Fukushima . |
| 4,509,219 | 4/1985 | Yagi . |
| 4,587,956 | 5/1986 | Griffin et al. . |
| 4,932,951 | 6/1990 | Liboff et al. . |
| 5,017,185 | 5/1991 | Baermann . |
| 5,304,111 | 4/1994 | Mitsuno et al. . |
| 5,344,384 | 9/1994 | Ostrow et al. . |

OTHER PUBLICATIONS

Jeannie Kever, Magnetic Pain Relief Attracts Interest.
Tectonic Magnets: The Invisible Massage That Let's You Feel a Difference.
John Latta, Magnets Banish Arthritis Pain, Heart Disease and Depression.
Magnetico Power Sleep Pads Advertisements.
Capovol, et al., Measurement and Analysis of Static Magnetic Fields That Block Action Potentials in Cultured Neurons, Biomagnetics, 1995 p. 197–206 vol. 16.
Sandyk, Chronic Relapsing Multiple Sclerosis: A Case of Rapid Recovery by Application of Weak Electromagnetic Fields, Intern. J. Neuroscience, 1995, pp. 223–242 vol. 82.
Sandyk, Improvement of Right Hemospheric Functions in a Child With Gilles de la Tourette's Syndrome by Weak Electromagnetic Fields Intern. J. Neuroscience, 1995, pp. 199–213 vol. 81.
Wulf, What's the Attraction? Time, 1997 p. 81 vol. 150n6.
McEnroe, Magnet P.I., Men's Health, 1998, pp. 86–87 vol. 13n3.

*Primary Examiner*—Cary O'Connor
*Assistant Examiner*—Pamela Wingood
*Attorney, Agent, or Firm*—Mueller and Smith, LPA

[57] ABSTRACT

Apparatus for applying magnetic flux to tissue utilizing strip-shaped flexible polymeric permanent magnets. The magnets are reinforced with an adhesively applied tape and removably inserted into retainer pockets or channels formed within a support structure. In one embodiment, the support structure is formed of two flexible mat components which are sewn together to form the retention pockets. A wrist rest embodiment utilizes a thin flexible platform to support the magnetic components within retention channels in combination with a foamaceous support structure.

20 Claims, 4 Drawing Sheets

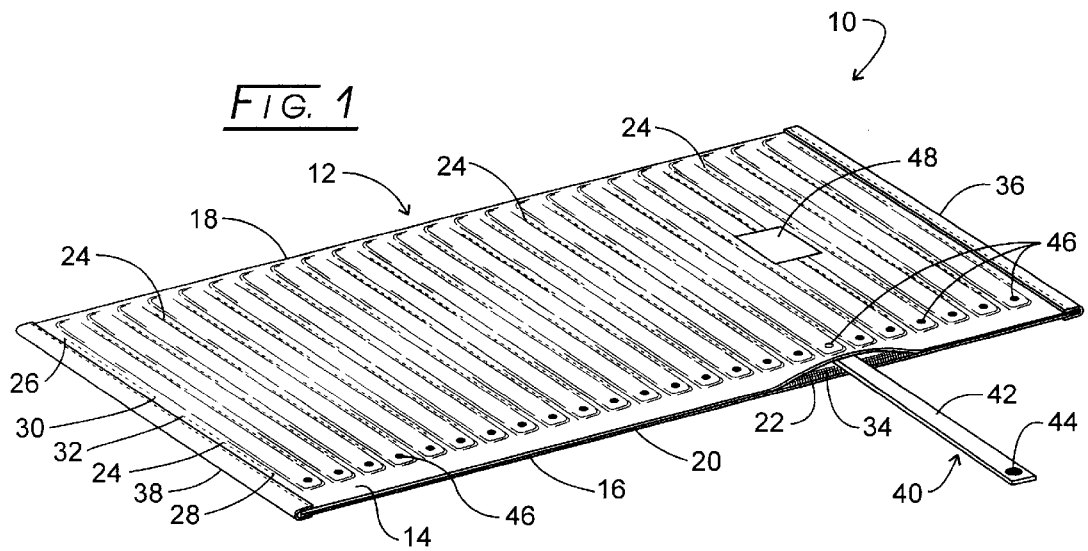
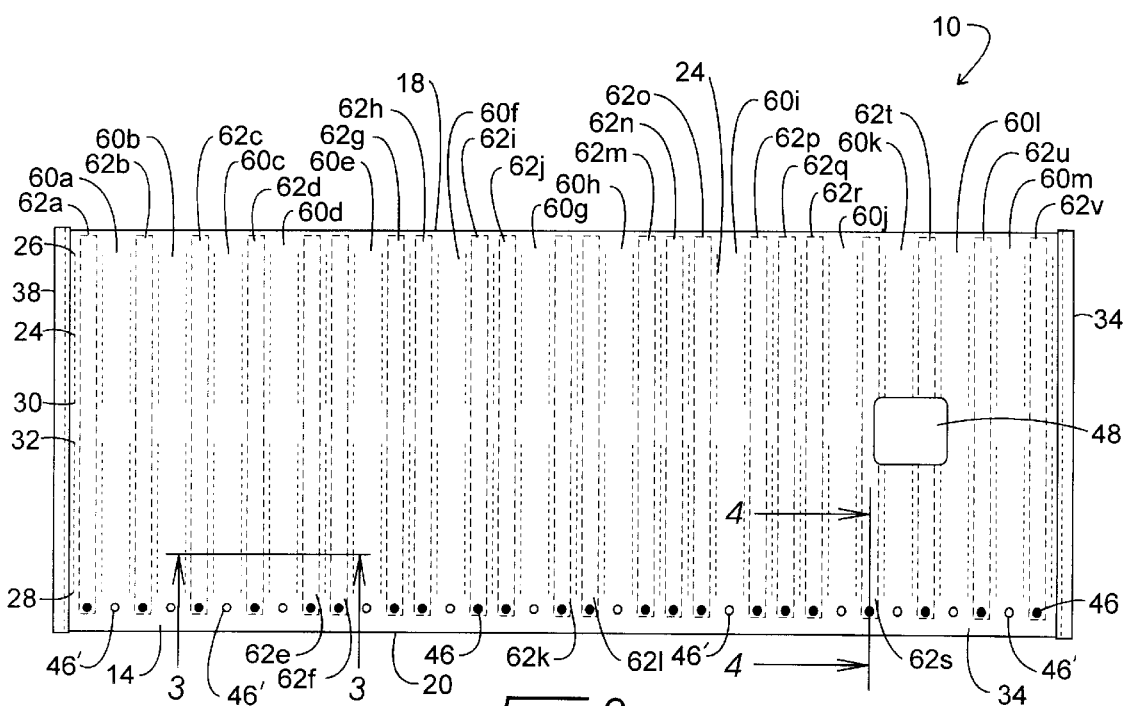

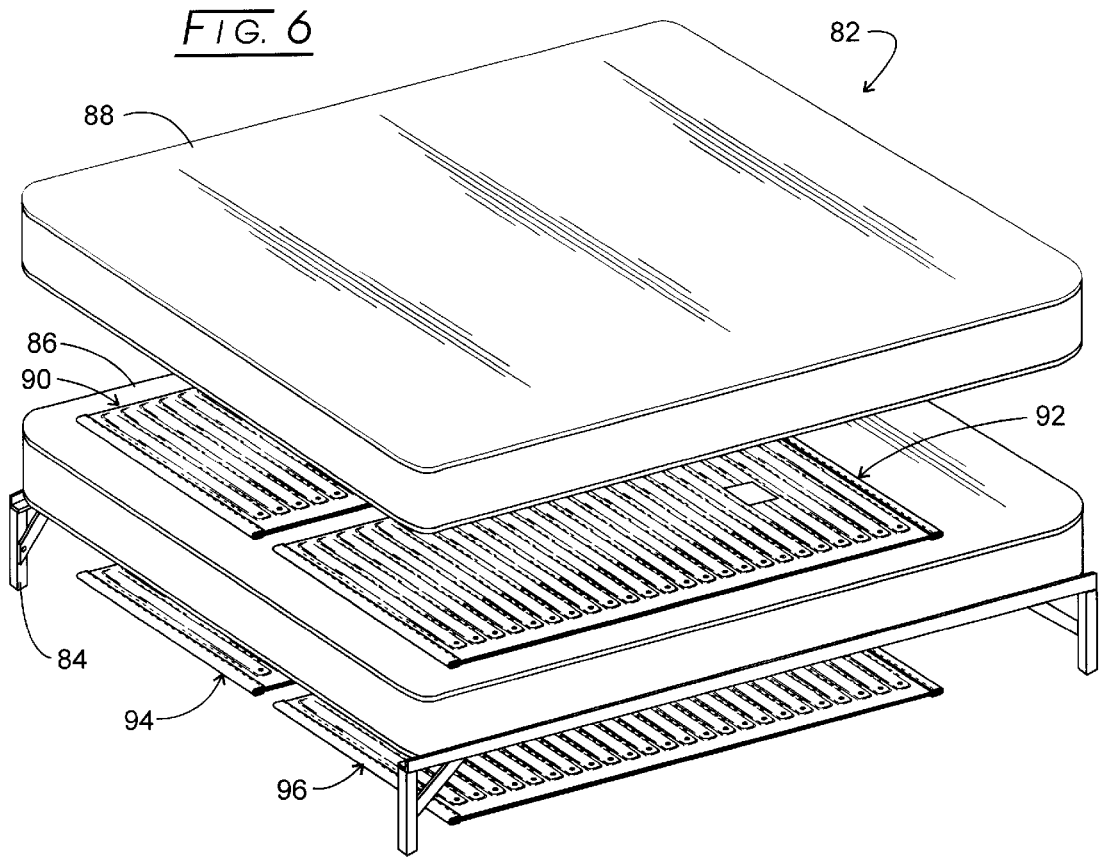
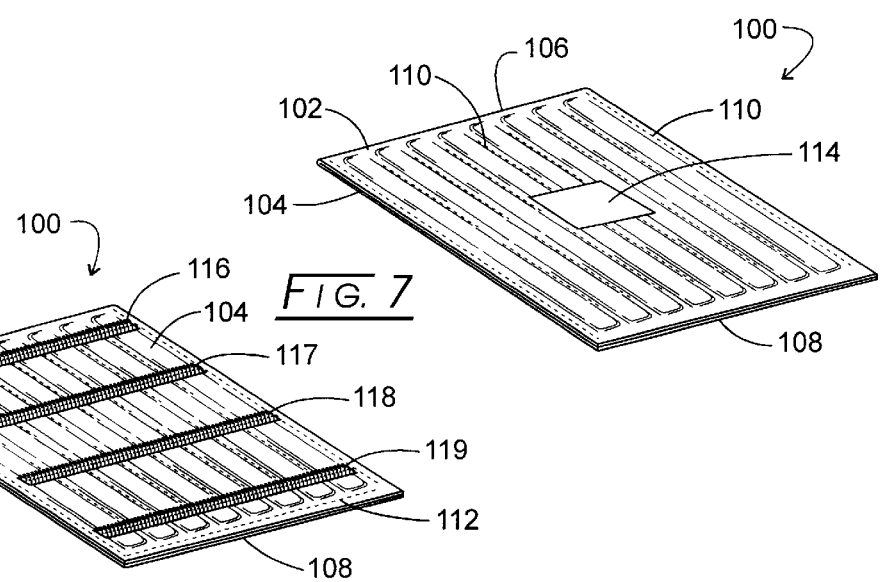
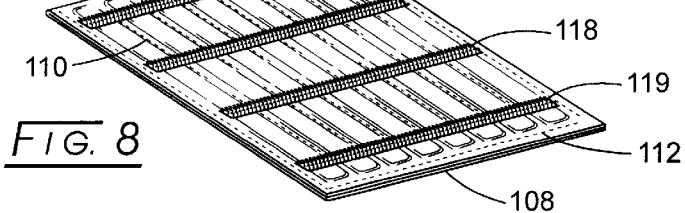

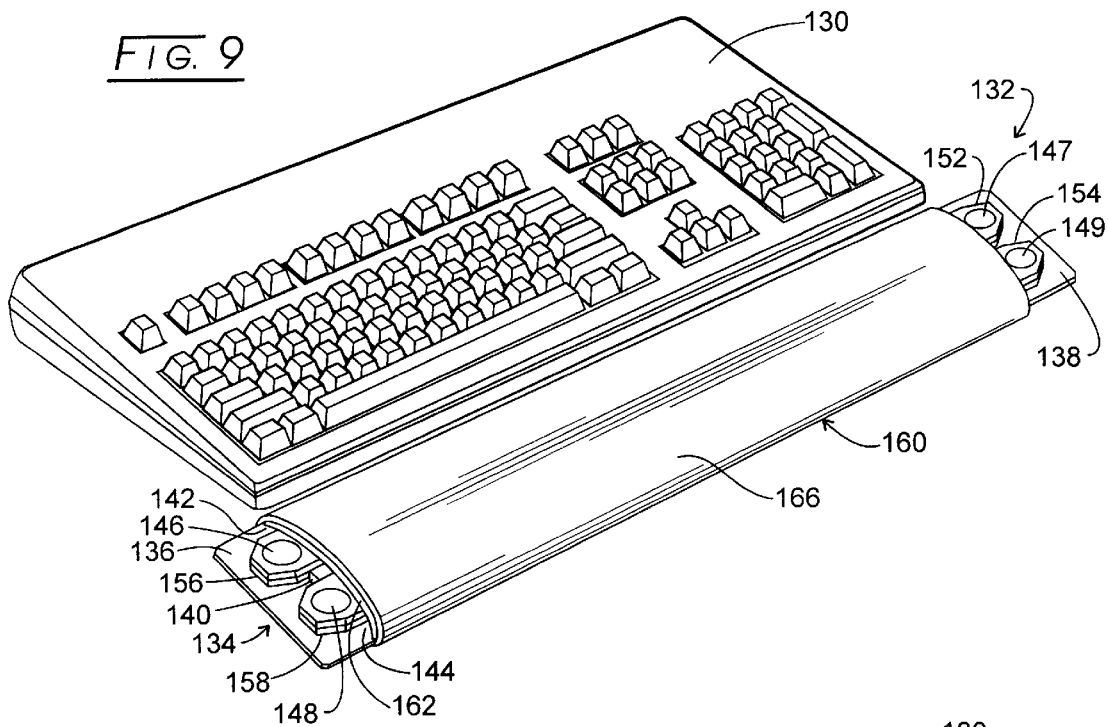
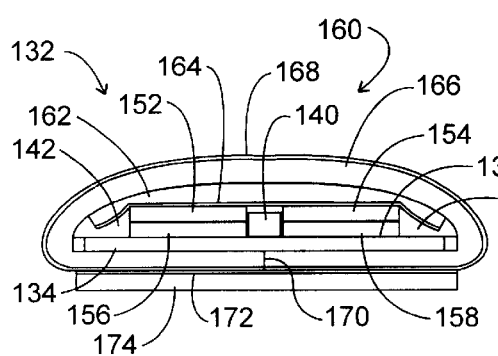
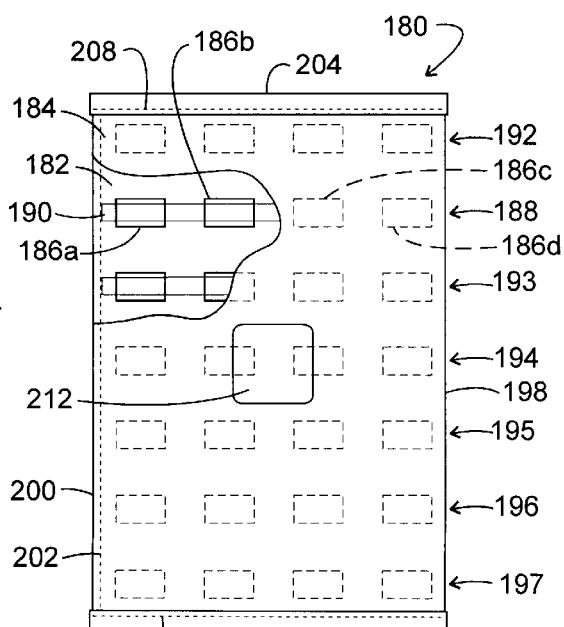

MAGNETIC FLUX APPLICATION TO TISSUE UTILIZING POLYMERIC STRIP-SHAPED PERMANENT MAGNETS

CROSS-REFERENCE TO RELATED APPLICATIONS

Not applicable

STATEMENT REGARDING FEDERALLY SPONSORED RESEARCH

Not applicable.

BACKGROUND OF THE INVENTION

Magnetic therapy has a long history dating back to the time of Cleopatra. It is alleged that the great Egyptian queen wore a magnet on her face to preserve her youthful appearance. The use of magnets has been known in the East for many years, but although there was a brief period of interest in the 1920's, magnetic therapy has only recently received serious attention in the United States. Much of the modern interest has resulted from the use of magnets by NASA. Scientists at NASA began using magnets to treat astronauts who, after returning from space, complained of weakness. The use of magnets has also been the focus of particular attention in the area of professional sports, where such athletes as Steve Atawater, Hideki Irabu, and Jim Colbert endorse their use. Magnetic devices come in all shapes and sizes and are used to treat a variety of conditions. See:

1.) What's the Attraction? By Steve Wulf, *Time*, V150n6, p.81 (1997).
2.) Magnet, P. I., by Colin McEnroe, *Men's Health*, Vol. 13 No. 3 pp. 86–87, (1998).

There have been a number of theories advanced to explain how magnetic therapy works. One expert contends that all injuries generate positive magnetic fields and that application of a negative magnetic field relieves pain and speeds healing. Another theory proposed is that magnets stimulate red blood cells that contain iron. Another physician maintains that magnets placed on the body separate positive and negative ions in the blood which physically pushes the walls of blood vessels apart resulting in increased blood flow to the affected area. A final theory is that magnets electrically stimulate neurons, blocking signals that cause pain.

A number of recent studies have addressed the issue of magnetic therapy. The theory that magnets electrically stimulate neurons was the subject of a paper by A. V. Cavopol, et. al. This paper proposed a magnetic formalism of the magnetic field of a single, circular current loop. The biological effect of different arrays of permanent magnets was found to depend on the spatial variation of the fields. Other studies have been done examining the effects of magnetism in the fields of arthritis, multiple sclerosis and Tourette's syndrome. In these areas see:

3.) Measurement and analysis of Static Magnetic Fields that Block Action Potentials in Cultured Neurons, by A. V. Capovol, A. W. Wamil, R. R. Holocomb, and M. J. McLean, *Bioelectromagnetics*, vol. 16 pp. 197–206 (1995).
4.) Chronic Relapsing Multiple Sclerosis: A Case of Rapid Recovery by Application of Weak Electromagnetic Fields, by Reuven Sandyk, *Intern. J. Neuroscience*, vol. 82 pp. 223–242 (1995).
5.) Improvement of Right Hemispheric Functions in a Child with Gilles de la Tourette's Syndrome by Weak Electromagnetic Fields, by Reuven Sandyk, *Intern. J. Neuroscience*, vol. 81 pp. 199–213 (1995).

There are a number of different magnetic devices that are currently available. Most of these medical magnets range in strength and normally have a north pole on one side and a south pole on the other. These magnets may also be unipolar and are available as discs that are taped to the afflicted area, inserts that may be worn in shoes or wrap that may bandage the area. A magnetic bed has also designed which contains A substantial number of discrete magnets. These beds are somewhat expensive and the necessity of purchasing a new bed is burdensome. Magnetic mattress pads are also available containing substantial numbers of discrete magnets permanently bound in a pattern. In general, the bed associated devices now marketed are bulksome, difficult to maneuver by the user, typically non-adjustable in terms of magnetics by the user and expensive to ship.

BRIEF SUMMARY OF THE INVENTION

The present invention is addressed to apparatus and method for carrying out the application of magnetic flux to tissue. The apparatus incorporates thin, strip-shaped polymeric permanent magnets which, in a preferred embodiment, are insertable within or removable from retention pockets or channels. These channels or pockets are formed within a support structure. In one embodiment, that support structure is formed from two thin, flexible mat components which are mutually overlaid in registry. The retention pockets are formed at the internal interface between these overlapping mat components by forming sewn seams along parallel, spaced apart connector lines. Access to the thus formed retention pockets is by the opening of a fastener closed boarder region of the support structure.

By spacing the insertion of the strip-shaped permanent magnets, the magnetic flux density of the treatment zone of the apparatus may be adjusted by the user. Similarly, by aligning two of the strip-shaped permanent magnets in series coupled polarity, the concentration of magnetic flux may be selectively increased by the user.

In order that the surface based polarity of the strip-shaped polymeric magnets may be identified by the user, a color component based visible indicia is placed upon a surface of desired polarity of each magnet. When a magnet is installed within a retention pocket, the indicia are visible through an open port formed within an appropriate one of the mat components. To achieve a desired flexibility of the polymeric, strip-shaped magnets, while avoiding their breakage, reinforcing adhesive tape is applied to the opposite flat surfaces thereof.

Transfer and storage of the flexible mat component-based embodiment of the apparatus of the invention is substantially simplified inasmuch as the structuring of them is such as to permit their being rolled up over a conventional mailing tube.

In another embodiment of the invention, the polymeric strip-shaped permanent magnets are incorporated within a cushion defining structure having the shape of a conventional wrist rest utilized by operators of computer terminals and the like. In this embodiment, a rigid plastic support member is employed in conjunction with a separator to define two retention channels which are overlaid and further defined by a foamaceous cushion structure. The plastic support structure extends beyond the cushion structure to define platform regions upon which the strip-shaped magnets protrude to reveal the noted color component based indicia identifying a desired surface polarity. This structure may be shortened to provide a wrist rest for utilizing a computer mouse or the like.

Other objects of the invention will, in part, be obvious and will, in part, appear hereinafter.

The invention, accordingly, comprises the apparatus and method possessing the construction, combination of elements, arrangement of parts and steps which are exemplified in the following detail description.

For a fuller understanding of the nature and objects of the invention, reference should be had to the following detailed description taken in connection with the accompanying drawings.

BRIEF DESCRIPTION OF THE DRAWINGS

FIG. 1 is a pictorial view of one embodiment of apparatus according to the invention showing the procedure for inserting a polymeric strip-shaped permanent magnet within a retention pocket;

FIG. 2 is a top view of the apparatus of FIG. 1;

FIG. 6 is a perspective view showing a conventional bed and the placement of apparatus according to FIG. 1 with respect to the components thereof;

FIG. 7 is a perspective view of another embodiment of the apparatus of the invention;

FIG. 8 is a perspective, underside view of the apparatus of FIG. 7;

FIG. 9 is a perspective view showing another embodiment of apparatus according to the invention in conjunction with a computer keyboard;

FIG. 10 is a side view of the apparatus of the invention shown in FIG. 9; and

FIG. 11 is a top view of another embodiment of apparatus according to the invention with portions broken away to reveal internal structure.

DETAILED DESCRIPTION OF THE INVENTION

Figure 3:
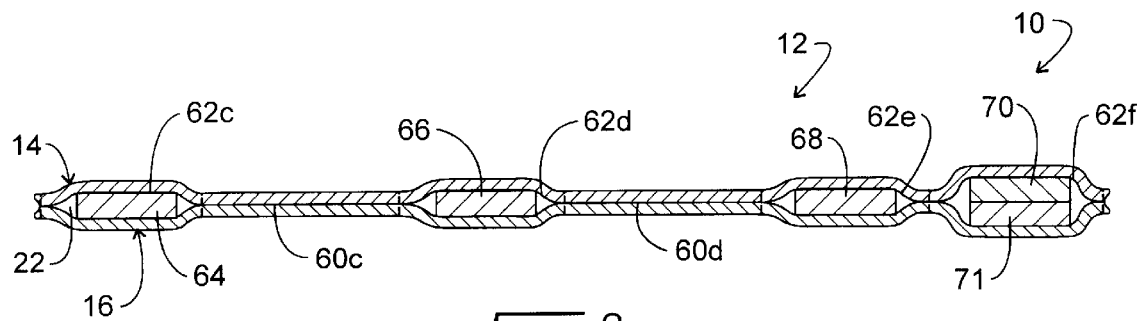
FIG. 3 is a partial sectional view taken through the plane 3—3 shown in FIG. 2.

A salient aspect of the magnetic flux application apparatus of the invention resides in its flexibility and portability even though relatively large treatment zones may be developed. In the latter regard, these treatments zones may be of a size commensurate with the size of a twin bed. They can be positioned between the mattress and spring components of such bed with ease and, because of the flexibility inherent in them, their presence is essentially unknown to the user.

Referring to FIG. 1, the latter large zone implementation of the apparatus is represented generally at 10. Apparatus 10 has the capability of developing a treatment zone 12 commensurate with the size of a twin bed, i.e., about 27 inches times 60 inches. As will be apparent, even larger sizes are readily constructed and the principles of the invention can be applied in constructing much smaller flux application devices. The apparatus 10 is formed of two flexible mat components 14 and 16 which are mutually overlaid in registry. In the embodiment shown, the mat components 14 and 16 are formed of a single piece of fabric or suitable flexible material which is folded at border 18 and the edges are overlaid in registry at the opposite border 20. This develops an interface 22 between the mutually inwardly facing surfaces of the components 14 and 16. While a variety of fabrics or materials can be used for the mat components 14 and 16, a preferred one is a polymeric upholstery material, for example, Lona SF oil and stain resistant F/R MVSS 302 white upholstering material which is fleece backed FRo/s NWV-FB 40/N woven material marketed by Vernon Plastics Company, of Haverhill Mass. 01835. Mat components 14 and 16 are connected together, inter alia, along an array of parallel connection lines which are spaced apart along the lengthwise dimension of apparatus 10 and represented in the figure by sewn seams certain of which are shown at 24. Note that these sewn seams are regularly spaced apart along the lengthwise dimension of the apparatus 10 and that they do not extend all the way to the borders 18 and 20. For example, looking at the end of seam 24, note that it extends only to position 26 located inwardly from border 18. Similarly, the seam 24 extends only to position 28 located inwardly from the border 20. Additionally, seam 24 is not continuous between positions 26 and 28. In this regard, it extends from position 30 to position 26 and from position 32 to position 28. This facilitates the activity of sewing during manufacture. A relatively robust thread is preferred for forming the sewn seams 24. For example, a thread identified as: "thin high strength polyester Metrosenc Plus Art 1155, No. 100 col. Manufactured by Mettler Company of Germany and distributed in the United States by Jo-Anne Fabric having an outlet, for example, in Columbus, Ohio. Thus sewn, the seams 24 function to define an array of parallel retention pockets which are accessible along border 18. To permit this access, as well a; to provide for fastening the mat components 14 and 16 together at border 20, a fastener arrangement is attached to one of the mat components 14 or 16. In this regard, it may be observed that a fastener 34, is connected to the inwardly disposed surface of mat component 16. The fastener 34 preferably is provided as a tape-like array of polymeric fabric engaging hooks which will engage the fabric or fleece inward surface of the mat component 14. Such fasteners are marketed under the trade designation "Velcro". A preferred material is identified as Velcro brand Marque Marca ¾ inch stickyback and sewable tape marketed by Velcro U.S.A., Inc. of Manchester N.H. This tape is both sewn and adhesively adhered to the inner surface of mat component 16 The longitudinally opposite ends of mat components 14 and 16 are sewn together using an edge binding as shown at 36 and 38. Such edge binding may be provided, for example as double fold quilt binding PC 13 117 706 which is 50% polyester and 50% cotton and manufactured by William E. Wright Co., West Warren Mass. 01092.

Magnetic flux density is developed at treatment zone 12 by the insertion of a plurality of thin, strip-shaped permanent magnets into the channels or pockets defined by sewn seams 24. One such permanent magnet is depicted in general at 40 as being inserted within a pocket or channel, access to the pocket being provided by the opening of the border interface 22 by pulling the upper mat component 14 from the fastener 34. For this embodiment, the permanent magnet 40 is both thin and elongate, extending substantially across the widthwise extent of apparatus 10. Preferably, these permanent magnets 40 are formed of a flexible polymeric material, each having a magnetic field and exhibiting a predetermined polarity at a surface thereof, for example the upwardly disposed surface 42 of magnet 40. Magnets 40 may be provided, for example as high energy polymeric magnetic strips sold under the trade designation "Duraflex" rated at 1.4MGOe-No. 1 polarity marketed by Drua Magnetics, Inc., 5500 Schultz Drive, Sylvania Ohio 43560. Preferably, each magnet as at 40 is reinforced with a reinforcing tape which is adhesively adhered to both sides of it, i.e., surface 42 and the lower surface opposite it. In this regard, a glass reinforced filament mailing tape having a width for example of ¾ inch may be employed. Such tapes are marketed by Minnesota Mining and Manufacturing Company, 3-M Consumer Stationary Division, St. Paul Minn. 55133. Experience with the polymeric elongate strip-shaped magnets as a 40 showed that they may break when flexed. This breakage is substantially reduced through the use of the reinforcing tape as described.

Positioned upon the upwardly disposed surface 42 of permanent magnet 40 is a visible indicia present as a colored disc or dot 44. Indicia 44 identifies the surface 42 as the surface of polarity-based interest, and functions to provide a visual cue assuring that the magnet 40 is inserted within the apparatus 10 in the correct polarity orientation. The colored discs 44 may be provided as gummed paper discs, for example: Red Glow 05467 T5467, ¾" diameter marketed by the Avery Division of Avery Dennison, Inc., Diamond Bar, Colo, 91765. To provide additional assurance that the magnets as at 40 are in this proper polarity orientation, small circular ports, certain of which are identified at 46 are formed inwardly from the border 20 within the upper mat component 14. Thus, when a magnet 40 is fully inserted within the apparatus 10, the colored disc 44 may be observed as a visual cue through the corresponding port 46. Finally, to assure proper orientation, a label 48 carrying user instructions is fixed to the outwardly disposed surface of mat component 14. In general, it is desirable that the polarity orientation of the magnets as at 40 be such as to be in serial or reinforcing association with the earth's magnetic field.

Figure 4:
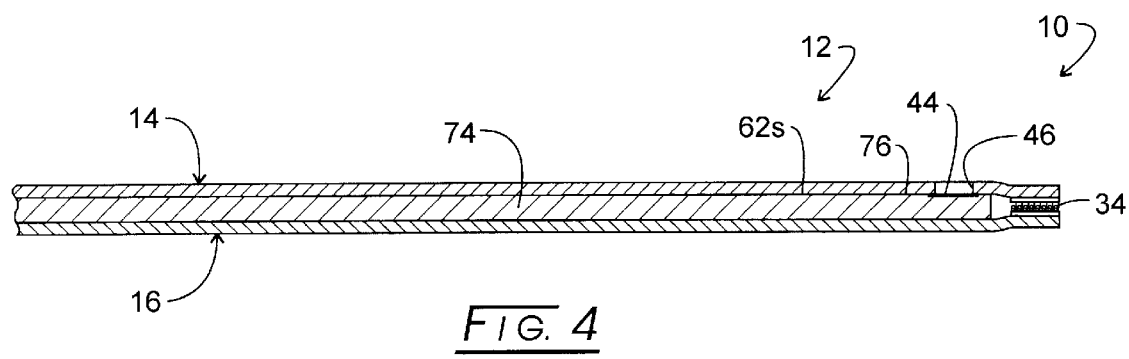
FIG. 4 is a partial sectional view taken though the plane 4—4 in FIG. 2.

The relatively simple insertability and removability of flexible polymeric permanent magnets as at 40 into and from the apparatus 10 provides a user opportunity for adjusting the magnetic flux density developed at treatment zone 12, as well as the magnetic flux concentration. Looking to FIG. 2, such flexibility is illustrated. In this regard, it may be noted that pockets identified at 60a–60m are empty, having no flexible strip magnets positioned therein. The corresponding ports thereof now represented at 46 with a prime are seen to carry no visual indicia indicating the presence of a magnet. However, the pockets 62a–62v carry the flexible strip permanent magnets. Accordingly, the color indicators 44 are readily seen through the ports 46. Looking additionally to FIG. 3, it may be seen that pocket or channel 62c supports a permanent magnet 64, while the adjacent pocket 60c is unfilled. Similarly, pocket 62d supports a permanent magnet 66 while adjacent pocket 60d is empty. Next, may be seen at pocket 62e supports a permanent magnet 68 and it may be noted, however, that pocket 62f supports two superimposed permanent elongate magnets 70 and 71. In this regard, the spacing between sewn seams 24 is selected so as to permit this insertion and support of two or more magnets which are aligned in series coupled polarity. With such an arrangement, the concentration of flux emanating from these combined magnets 70 and 71 is selectively increased by the user. By providing for empty pockets or channels as seen at 60c and 60d, the overall flux density of the treatment zone 12 can be adjusted downwardly in value. FIG. 4 reveals that pocket 62s carries a permanent magnet 74. This figure further shows the port 46 extending through the upper surface 76 of the magnet 74 so as to permit viewing of the color indicator 44. The figure also shows the connector 34.

Figure 5:
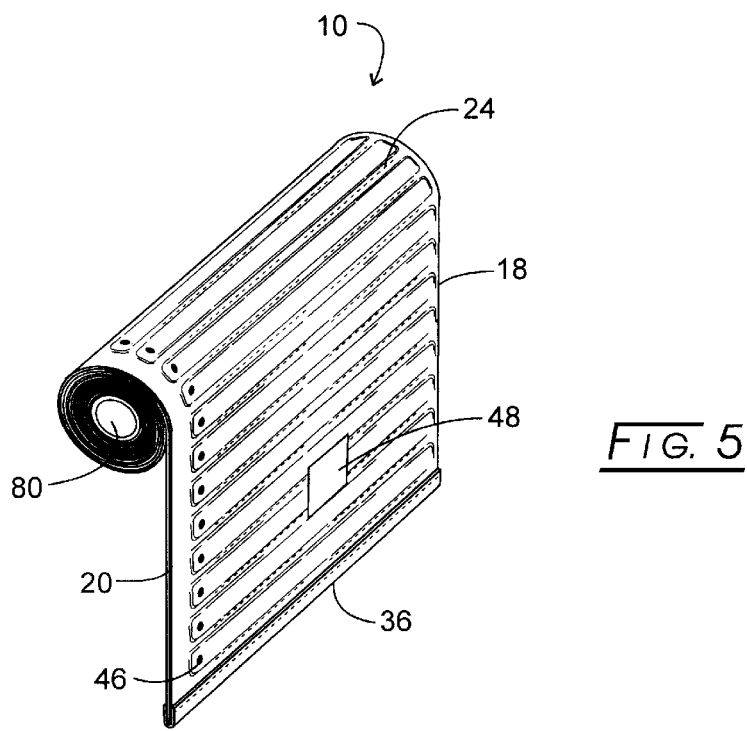
FIG. 5 is a perspective view of the apparatus of FIG. 1 being rolled about a tube support.

Looking to FIG. 5, an advantage of the flexibility and flatness of the apparatus 10 is revealed with respect to storing and shipping it. In the figure, it may be seen that the apparatus 10 is readily wrapped about a tube 80 for purposes of storage and shipping. Tube 80 may be, for example a conventional cardboard mailing tube.

Looking to FIG. 6, the utilization of apparatus 10 in connection with a typical bed is revealed. In the figure, a bed represented generally at 82 is seen to be comprised of a lower frame 84, a spring assembly 86 and a mattress 88. For this arrangement, typically, the magnetic flux applying apparatus 10 is positioned between the spring assembly 86 and mattress 88. This is demonstrated by the magnetic flux application devices 90 and 92. These devices also have been found to be effective if placed beneath the spring assembly 86 or, in the case of waterbeds, beneath the waterbed mattress. Such positioning is represented by the flux applying devices 94 and 96.

The apparatus 10 can be configured in more diminutive size for other applications, an example being for use with a seat or as a foot rest. For the latter application, a size of, for example thirteen inches by ten inches has been found to be appropriate. Such an embodiment is represented in FIGS. 7 and 8 illustrated generally as an apparatus 100. Apparatus 100 is formed, as before of two flexible mat components 102 and 104 which are mutually overlaid in registry. For this embodiment, a singular piece of material or fabric is utilized which is folded at border 106 and the edges of which are aligned at opposite border 108. Pockets or channels are defined by sewn seam parallel connection lines certain of which are represented at 110. A fastener is attached at border 108 both adhesively and by sewn seam 112 as shown in FIG. 8. Elongate strip-shaped permanent magnets, preferably of the above identified polymeric or plastic variety are inserted within pockets or channels defined by the sewn seams 110 and are accessed for insertion or removal through a fastener (not shown) at border 108. As before, an instructional label 114 is provided to identify the properly upwardly directed side of the apparatus 100. Because of its more diminutive size, the device 100 the fastening arrangement is provided at upon the outwardly disposed edge of mat component 104. These fastening assemblies may be provided as the earlier described polymeric fabric engaging hooks marketed under the trade designation "Velcro". Four strips of such fasteners are illustrated at 116–119.

Looking to FIGS. 9 and 10, another embodiment of the apparatus of the invention wherein it is employed in combination with the physical support of a component or components of the human anatomy is illustrated. In FIG. 9, a conventional computer terminal keyboard is represented at 130. The lengthwise size of keyboards as at 130 may vary from manufacture to manufacture, but typically, they will have a length of about 19 inches. The height of the keyboard at its forward edge typically is about ¾ inch. Many users of keyboards as at 130 operate them in conjunction with a soft elongate wrist support which is positioned immediately before the keyboard. In the present embodiment, a wrist support is provided, however, in conjunction with the thin, flexible polymeric permanent magnets utilized with the invention. In FIG. 9, such a wrist support is represented in general at 132. As seen additionally in FIG. 10, the support 132 is formed having an elongate, thin support member 134 which extends outwardly a distance of about one inch at either side of a cushion support 160 to define platform regions shown in FIG. 9 at 136 and 138. An elongate separator 140 is positioned between the two platform surfaces 136 and 138 generally centrally upon the support member 134. Separator 140, preferably, will be formed of a thin brush-like material which is adhesively attached to the upper surface of the port 134. A preferred embodiment for this separator is conventional weather stripping having an upwardly extending fibrous brush configuration. The separator 140 defines two oppositely disposed retention channels 142 and 144 which slidably receive thin elongate polymeric flexible strip-shaped permanent magnets. As before, these magnets are reinforced with an adhesive-backed flexible tape (not shown) and further carry the disc or dot shaped visible indicia represented as color components, four of which are seen in FIG. 9 at 146–149. Components 146 and 147 are seen to be adhesively adhered to strip-shaped permanent magnet 152, while components 148 and 149 are adhered to strip-shaped permanent magnet 154. As before, the color components 146-149 identify a surface of predetermined polarity of the strip magnet. In the embodiment shown, each of the retention channels 142 and 144 is utilized to retain two of such strip magnets arranged in reinforcing or series coupled polarity. In this regard, a strip-shaped permanent magnet 156 is positioned beneath magnet 152 and a strip-shaped magnet 158 is positioned beneath magnet 154.

FIG. 10 reveals that the assemblage of support member 134 separator 140 and strip-shaped permanent magnets 152, 154, 156 and 158 is wrapped with a fabric sided foamaceous material to form a pliant support represented generally at 160. FIG. 10 reveals an elongate inner strip of such cloth-backed foam material at 162 positioned over separator 140 and support 134 to further define the retention channels 142 and 144. Such cloth backing 164 of material 162 is seen in the figure to be facing downwardly, an arrangement which facilitates the slidable insertion of the strip magnets. Wrapped around the assemblage is another elongate strip of such pliant cloth-backed foamaceous material as at 166. The material at 166, however, is oriented such that its cloth backing 168 is upwardly disposed. The ends of the material strip 166 are brought together at a seam 170 and retained together using an adhesive tape. Attached over the seam 170 and across the bottom of the assemblage is another strip of the cloth-backed foamaceous material 172. Strip 172 is oriented such that its cloth backing 174 is upwardly disposed and its foamaceous component is downwardly disposed. The strip 172 is attached to the downwardly disposed, cloth-backing of strip 166 using an adhesive tape (not shown) or a spray adhesive such as "3M Super 77" marketed by Minnesota Mining and Manufacturing, Inc., of St. Paul Minn.

FIG. 9 reveals that the ends of the strip-shaped magnets 152, 154, 156 and 158 protrude outwardly from the pliant support 160 and are supported at the platform regions 136 and 138 of support 134. This facilitates their insertion within the pliant support or cushion component 160 and provides for operator observation of the color components 146–150 to assure proper polarity orientation of the permanent magnets. In general, the thickness of the pliant support 160 will be about ¾ inch. The material forming it may be provided, for example as Alpine Headliner marketed by Guilford Mills, Inc. of Greensboro N.C.

As an alternative to the cloth-backed foamaceous material 172, the bottom surface of the pliant support 160 may be sprayed with a friction promoting material. Wrist support 132 also may be manufactured with a foreshortened lengthwise extent. With this structure it may be employed in conjunction with a computer mouse or the like. For such an embodiment, the lengthwise extent of support member 134 is reduced to about six inches.

Referring to FIG. 11, another embodiment utilizing the polymeric, thin, strip-shaped flexible permanent magnets in a less expensive structuring is revealed in general at 180. The apparatus 180, while utilizing the flexible plastic magnets, does so in a manner wherein the flux concentration and flux density of the treatment zone of the apparatus cannot be adjusted to suit the needs of the user. However, advantage is taken of the flexible, polymeric magnet structures. In the figure, as before, two flexible mat components are provided as at 182 and 184. However, positioned upon the inwardly disposed surface of mat component 182 there are adhesively mounted a plurality of foreshortened magnet components four of which are seen at 186a–186d. The discrete permanent magnet components 186a–186d are mutually aligned along their lengths and spaced apart end-to-end to define a magnet row 188. Retention of the magnets 186a–186d to the inward surface of mat component 182 is preferably provided with a double sided adhesive tape strip as shown at 190 or in conjunction with magnet row 188. The remaining magnet rows of the apparatus 180 as at 192-197 are formed in the same fashion. Over the magnet rows, 188 and 192–197 then there is positioned the interior surface of mat component 184. As before, the mat components 182 and 184 are folded together from a single piece at border 198 and their edges are brought into registry or into alignment at border 200. The edges at border 200 are attached together by a sewn seam represented at 202, while the lengthwise edges of the components 182 and 184 are connected together, as before, utilizing edge binding as at 204 and 206 shown attached by respective sewn seams 208 and 210. The double sided adhesive tape as at 190 may be provided, for example as a type 665 marketed by the 3-M Commercial Office Supply Division of Minnesota Mining and Manufacturing Company, Inc., of St. Paul, Minn. To indicate the polarity developed by the magnets of the apparatus 180, a label or the like as at 212 may be provided on the outwardly disposed surface of mat component 184.

Since certain changes may be made in the above apparatus and method without departing from the scope of the invention herein involved, it is intended that all matter contained in the above description or shown in the accompanying drawings shall be interpreted as illustrative and not in a limiting sense.

What is claimed is:

1. Apparatus for carrying out treatment of tissue by the application of magnetic flux of predetermined concentration and polarity, comprising:

first and second flexible mat components mutually overlaid in registry having a first dimension extending between first and second borders;

said first and second mat components being connected together along two, parallel connection lines oriented normally to said first and second borders to define a retention pocket having an opening at said first border;

a thin strip-shaped permanent magnet having a magnetic field and exhibiting said predetermined polarity at a surface thereof, slideably inserted within said retention pocket with said surface exhibiting said predetermined polarity being adjacent said first flexible mat; and visible indicia located at said first flexible mat indicating said polarity.

2. The apparatus of claim 1 in which said permanent magnet is a flexible polymeric magnet.

3. The apparatus of claim 2 in which said permanent magnet includes a flexible tape reinforcing component adhesively connected to a said surface thereof.

4. The apparatus of claim 1 in which:

said first and second mat components are formed of a flexible polymeric material; and said first and second mat components are sewn together along at least a portion of said connection lines.

5. The apparatus of claim 1 in which said visible indicia comprises:
a viewing port formed within said first flexible mat; and
a color indicator component positioned upon said magnet at said surface and located to be visible at said viewing port when said magnet is within said retention pocket.

6. The apparatus of claim 1 including fastening means for manually parting and closing said first and second mats at said first border to access said retention pocket.

7. The apparatus of claim 6 in which said fastening means comprises an array of polymeric fabric engaging hooks attached to the inwardly disposed surface of a said first or second flexible mat component adjacent said opening at said first border.

8. The apparatus of claim 1 including an array of fabric engaging hooks attached to the outwardly disposed surface of said second flexible mat component.

9. Apparatus for carrying out treatment of tissue by the application of magnetic flux of predetermined density and polarity, comprising:
first and second flexible mat components mutually overlaid in registry, having a widthwise dimension extending between first and second borders and a lengthwise dimension extending normally to said widthwise dimension between first and second edges to provide a treatment zone;
said first and second mat components being connected together along an array of parallel connection lines spaced apart along said lengthwise dimension to define an array of parallel retention pockets having an opening at said first border;
a plurality of thin, strip-shaped permanent magnets, each having a magnetic field and exhibiting said predetermined polarity at a surface thereof, each being slidably inserted within a select one of said retention pockets with said surface exhibiting said predetermined polarity being adjacent said first flexible mat component to establish said predetermined magnet flux density within said zone; and
visible indicia located at said first flexible mat indicating said polarity.

10. The apparatus of claim 9 in which each of said permanent magnets is a flexible polymeric magnet.

11. The apparatus of claim 10 in which each said permanent magnet includes a flexible tape reinforcing component adhesively connected to at least one surface thereof.

12. The apparatus of claim 9 in which said first and second mat components are connected together along said connection lines by sewn seams.

13. The apparatus of claim 12 in which each of said sewn seams extend from a location commencing a select distance inwardly from said first and second borders.

14. The apparatus of claim 9 in which said visible indicia comprises:
a viewing port formed within said first flexible mat in visual communication with each said retention pocket; and
a color indicator component positioned upon each said magnet at said surface and located to be visible at said viewing port when said magnet is within said retention pocket.

15. The apparatus of claim 9 including fastening means for manually parting and closing said first and second mat components at said first border to access each said retention pocket.

16. The apparatus of claim 15 in which said fastening means comprises an array of polymeric fabric engaging hooks attached to the inwardly disposed surface of a said first or second flexible mat component adjacent said opening at said first border.

17. Apparatus for applying magnetic flux of predetermined flux concentration and polarity to a component of animal anatomy in combination with the physical support of such component, comprising:
a pliant cushion assembly having a lengthwise extent, a cushion thickness and a widthwise extent disposed normally to said lengthwise extent;
an elongate receptor channel within said cushion assembly located within said cushion thickness;
a thin, strip-shaped polymeric permanent magnet having a magnetic field and exhibiting said predetermined polarity at a surface thereof, positioned within said retention channel with said surface exhibiting said predetermined polarity having a known orientation; and
visible indicia observable upon said apparatus identifying said known orientation.

18. The apparatus of claim 17 in which:
said component of animal anatomy is the human wrist;
said cushion assembly lengthwise extent corresponds with the lengthwise extent of a keyboard and said widthwise extent corresponds with the size of a human wrist; and
said receptor channel extends along said lengthwise extent.

19. Apparatus for applying magnetic flux of predetermined concentration and polarity to tissue, comprising:
first and second flexible mat components mutually overlaid to define an interface having a dimension extending between first and second borders;
at least two polymeric, thin, strip-shaped flexible permanent magnets of length extending between oppositely disposed ends, each having a magnetic field and exhibiting said predetermined polarity at a surface thereof, positioned upon said second mat component at said interface in mutual alignment along their lengths and spaced apart end-to-end to define a magnet row of discrete permanent magnet extending substantially between said first and second borders, said surface of each said magnet being oriented toward said first mat component;
connecting means for adhesively fixing said magnets at said interface; and
visible indicia at said first mat component visually identifying said surface orientation.

20. The apparatus of claim 19 in which said connecting means comprises a length of tape carrying an adhesive and extending upon said magnets and at least one said first and second mat component in adhesively fixing relationship.

* * * * *